United States Patent [19]
Foret

[11] Patent Number: 5,832,361
[45] Date of Patent: Nov. 3, 1998

[54] TREATMENT OF FLUIDS WITH ELECTROMAGNETIC RADIATION

[76] Inventor: Todd Leon Foret, 127 N. Morein St., Ville Platte, La. 70586

[21] Appl. No.: 609,731

[22] Filed: Mar. 1, 1996

[51] Int. Cl.⁶ .................................................. B01J 19/08
[52] U.S. Cl. ...................................... 422/186; 250/432 R
[58] Field of Search ............................... 422/186.3, 186; 204/157.15, 157.3, 158.2; 250/432 R

[56] References Cited

U.S. PATENT DOCUMENTS

| | | | |
|---|---|---|---|
| 2,705,219 | 3/1955 | Heiskell et al. | 204/128 |
| 3,201,337 | 8/1965 | Eichelberger et al. | 204/157 |
| 3,772,172 | 11/1973 | Zhagatspanian et al. | 204/157.1 |
| 3,826,920 | 7/1974 | Woodroffe et al. | 250/373 |
| 4,397,823 | 8/1983 | Dimpfl | 423/210 |
| 4,427,636 | 1/1984 | Obenshain | 422/186.07 |
| 4,622,115 | 11/1986 | O'Neill | 204/157.41 |
| 4,803,365 | 2/1989 | Krause et al. | 250/461.2 |
| 4,948,980 | 8/1990 | Wedekamp | 250/504 R |
| 5,120,450 | 6/1992 | Stanley, Jr. | 210/748 |
| 5,124,131 | 6/1992 | Wekhof | 422/186.3 |
| 5,200,156 | 4/1993 | Wedekamp | 422/186.3 |
| 5,413,768 | 5/1995 | Stanley, Jr. | 422/186.3 |

Primary Examiner—Charles T. Jordan
Assistant Examiner—John R. Hardee
Attorney, Agent, or Firm—Warner J. Delaune

[57] ABSTRACT

A device is provided for irradiating a fluid containing molecules subject to photolytic fission within a conduit, wherein the conduit includes a first opening and a longitudinal axis, the device comprising a valve fluidically connected to the first opening, the valve having a passageway leading to a second opening; a first optical member sealing the second opening; and an electromagnetic radiation (EMR) source positioned relative to the first optical member such that the EMR is directed, preferably along the longitudinal axis, through the first optical member and the passageway and into the conduit when the valve is an open position; wherein the first optical member is constructed from a material which is permeable to the EMR. The EMR source is preferably adapted to emit EMR at a wavelength sufficient to cause photolytic fission of the selected molecules in the fluid, and more preferably adapted to emit EMR at a wavelength sufficient to cause photolytic fission of nitrogen trichloride, diatomic chlorine, or both. Also, an air purging device is optionally provided near the valve so that fluid may be purged from the vicinity of the first optical member when the valve is being closed. Additional optical members, such as a filter, may be optionally disposed between the first optical member and the EMR source.

8 Claims, 5 Drawing Sheets

TREATMENT OF FLUIDS WITH ELECTROMAGNETIC RADIATION

BACKGROUND OF THE INVENTION

I. Technical Field

This invention relates generally to devices and methods used to treat fluids with electromagnetic radiation, and more particularly to the treatment of chlorine with electromagnetic radiation to remove hydrogen and nitrogen trichloride.

II. Prior Art

Irradiating fluids with electromagnetic radiation (EMR), particularly within the 4 nanometer (nm) to 400 nm wavelength (or ultraviolet) (UV) range is well known and well documented. For instance, UV sterilization of water is commonly achieved using a 254 nanometer UV radiation source. Many commercial and industrial applications for UV sterilization are increasing due to their effectiveness in destroying microbiological organisms, as well as in deozonization processes. In addition, UV radiation is often used to reduce Total Organic Carbon (TOC) in a wide variety of substances. For example, a wavelength of about 185 nm is typically employed to reduce TOC in certain applications, such as in the manufacture of electronic microchips where ultra-pure water is required. Similarly, in many waste treatment plants the effluent has a high TOC, and lowering the TOC would be highly beneficial to the plant in meeting its permit discharge limits. Although many other applications of electromagnetic irradiation could be enumerated, the primary focus of the present invention is in the production of chlorine or chlorinated products, as will be further explained below.

Chlorine is produced by the electrolysis of melted sodium chloride or an aqueous solution containing sodium chloride (referred to as "brine"). The products of this chemical reaction are chlorine, hydrogen, oxygen and sodium hydroxide (or "caustic soda"). The hydrogen is continuously produced as an impurity in the fluid mixture and may range in concentration from about 0.5% to about 2% by volume. While much of the hydrogen combines to form sodium hydroxide, a residual amount typically remains within the chlorine wet gas. Since the electrolysis reaction is exothermic, the temperature of the chlorine wet gas leaving each electrolysis cell can be as high as 90° C. If hydrogen concentration approaches about 3%, a potentially explosive environment is created where chlorine is the oxidant, hydrogen is the fuel and the reaction temperatures cause a spontaneous, self-sustaining chain reaction.

To reduce the possibility of explosion due to the increasing hydrogen concentration, prior methods usually involved purging the fluid stream with dilution air. As a result, the hydrogen concentration is diluted to within acceptable limits as prescribed by plant operating procedures. However, the air purge has an adverse effect on plant capacity, because it necessarily reduces the volume of chlorine production. Moreover, although chlorine production is decreased, the plant must still operate at full compressor capacity, making it difficult to compensate for the decreased production levels.

Given the past inadequacies of air purging, modern methods of reducing hydrogen commonly involve irradiation of the liquid chlorine with UV or other levels of radiation. This process takes advantage of the fact that chemical chain reactions usually involve the formation of free radicals as intermediates. An example is the reaction of chlorine with hydrogen initiated by EMR. A chlorine molecule is first split into its constituent atoms:

$Cl_2 \rightarrow Cl\cdot + Cl\cdot$

These chlorine radicals react with hydrogen and with each other as follows:

$Cl\cdot + H_2 \rightarrow HCl + H\cdot$
$H\cdot + Cl_2 \rightarrow HCl + Cl\cdot$
$Cl\cdot + Cl\cdot \rightarrow Cl_2$ Thus, the hydrogen may be completely removed from the chlorine stream, in theory, by the application of suitable EMR which will maintain these chain reactions at the sacrifice of a relatively small amount of chlorine production.

Another by-product formed in the production of chlorine or chlorinated products is nitrogen trichloride. The presence of nitrogen trichloride within the chlorine stream is very dangerous at low concentrations and it explodes violently at temperatures above 90° C. Extensive studies have been conducted by members of The Chlorine Institute, Inc., in an effort to precisely determine the amount of nitrogen trichloride that can be considered unsafe. However, accurate and reliable information on the nature of this compound has been difficult to obtain. Thus, any means of decreasing nitrogen trichloride to the lowest possible level during the production of chlorine would be an extremely desirable safety measure. Toward this goal, a number of devices and processes have been developed over the years which involve subjecting the chlorine stream to UV radiation, which has proved more or less effective in reducing nitrogen trichloride.

In the early 1950's and 1960's many tests were conducted with UV radiation in an attempt to solve the hydrogen and nitrogen trichloride problems associated with chlorine production. For example, on Nov. 8, 1962, a paper was presented by C. R. Dilmore of PPG Industries, Inc., to the Chlorine Institute which discussed the success of ultraviolet lights in the reduction of nitrogen trichloride. U.S. Pat. No. 2,705,219 issued to Heiskell, et al., also discloses a process involving UV radiation to reduce nitrogen trichloride levels in which an elongated UV source is enclosed within a thimble and inserted into the chlorine stream. With respect to the reduction of hydrogen, A. G. Follows of Allied Chemical submitted a paper to The Chlorine Institute, Inc., on Feb. 2, 1966, regarding a case history which solved much of the hydrogen problem with an actual plant trial. This work was based in part on the disclosure of U.S. Pat. No. 3,201,337, issued to Eichelburger, et al., which also focused on the removal of hydrogen from chlorine gas by UV irradiation.

U.S. Pat. No. 4,948,980, issued to Wedekamp, discloses a system for UV irradiation of fluids, wherein a ring of external UV-radiation sources is directed toward the center of a tubular body constructed from a UV-permeable material. The claimed advantage of this type of arrangement is that the radiation is focused into the fluid traveling through the tubular body, thus increasing the radiation density in the treated fluid. Despite this perceived advantage, a major problem exists in that the flow line cannot be cleaned without shutting off that portion of the treatment system. Through prolonged exposure to chlorine, the internal surface of the tubular body will become cloudy and coated with a thin film of chlorine, sodium chloride and other contaminants, which impedes the transmission of UV light. The only alternative to shutting down the system is either: (1) installation of an internal wiper system, which is very expensive in terms of both labor and materials to install and maintain; or (2) the construction of one or more bypass lines, which carries the same disadvantages.

U.S. Pat. No. 5,200,156, also issued to Wedekamp, discloses a UV device which has been used effectively in several chlorine plant applications. That reference discloses a system comprising one or more UV-radiation sources which are protectively housed within a quartz or other UV-permeable enclosure. The UV sources are placed directly in the path of the fluid and perpendicular to fluid flow with the intention of maximizing the irradiation of the fluid with minimal radiation loss. Unfortunately, this system carries the same cleaning and shut-down disadvantages as seen in the '980 patent, because the radiation sources are directly in the flow path. Moreover, if the protective quartz tubing should ever break, the electrical UV-radiation source is exposed to the surrounding chemicals, creating a potentially explosive environment. In such an accident, quartz fragments will necessarily travel downstream within the fluid flow, possibly damaging expensive equipment as well.

From a review of the above mentioned references, it can be seen that the ideal EMR system should combine the following features: (1) effective irradiation of the fluid, (2) inexpensive and non-disruptive operation of the radiation sources, (3) minimization of safety hazards during operation of the system, (4) low-cost maintenance of EMR-permeable materials, and (5) simple installation and retrofitting procedures for existing treatment equipment. However, experience has shown that satisfaction of the first criterion usually means sacrificing one or more of the remaining design factors.

Although the prior devices and methods provide reduction of both hydrogen and nitrogen trichloride in modern plant operations, there are many EMR applications which do not require full irradiation of the fluid, i.e. exposure of all elements of the fluid flow to high intensity radiation. The production of chlorine is a case in point. Due to the extreme susceptibility of chlorine ($Cl_2$) to form free radicals in the presence of certain levels of EMR, coupled with the fact that an extensive and sustainable chain reaction between chlorine and hydrogen takes place under relatively slight EMR exposure conditions, the inventor has discovered that there is no need to subject the entire fluid to radiation. Instead, it is only necessary to irradiate a small region of the fluid sufficient to initiate and sustain the chain reaction. Such insight has made it possible to consider designs which easily satisfy the first criterion of the "ideal" EMR system, with resultant success in meeting the remaining criteria as well.

On the other hand, while full irradiation of the entire fluid volume may not be required, it is essential that the intensity of the EMR be such that the maximum number of chain reactions be initiated and sustained. For example, while the UV radiation produced by the prior art devices is of a wavelength sufficient to cause photolytic fission of the diatomic chlorine and the nitrogen trichloride, a relatively small level of radiation is imparted to the fluid due to the geometry of the EMR source and its power rating. Thus, an improved EMR system is needed which is capable of employing inexpensive, easily available EMR sources which emit the required EMR at a wavelength, focus and intensity effective in minimizing undesirable contaminants.

Therefore, the present invention, which will be described in detail below, provides superior EMR delivery to the fluid to be treated, safely isolates the EMR source from the fluid without interrupting the fluid flow, reduces costs associated with installing and maintaining the EMR sources, and installs easily into existing structures by using standard flanges already present within the piping system.

SUMMARY OF THE INVENTION

Therefore, it is an object of the present invention to provide a device for irradiating fluids which is capable of subjecting the fluid to EMR at a wavelength, focus and intensity that is superior to prior methods.

An additional object of the present invention is to provide a device for irradiating fluids which does not interrupt fluid flow.

Another object of the present invention is to provide a device for irradiating fluids which permits the isolation of the EMR source for maintenance without interrupting fluid flow.

Still another object of the present invention is to provide a device for irradiating fluids which can be easily installed via standard flanges which are typically used in fluid applications.

These and other objects and advantages of the present invention will no doubt become apparent to those skilled in the art after having read the following description of the preferred embodiments.

Therefore, a device for irradiating a fluid containing molecules subject to photolytic fission within a conduit, wherein the conduit includes a first opening and a longitudinal axis, the device comprising a valve fluidically connected to the first opening, the valve having a passageway leading to a second opening; a first optical member sealing the second opening; and an electromagnetic radiation (EMR) source positioned relative to the first optical member such that the EMR is directed, preferably along the longitudinal axis, through the first optical member and the passageway and into the conduit when the valve is in an open position; wherein the first optical member is constructed from a material which is permeable to the EMR. The EMR source is preferably adapted to emit EMR at a wavelength sufficient to cause photolytic fission of the selected molecules in the fluid, and more preferably adapted to emit EMR at a wavelength sufficient to cause photolytic fission of nitrogen trichloride, diatomic chlorine, or both. Also, an air purging device is optionally provided near the valve so that fluid may be purged from the vicinity of the first optical member when the valve is being closed. Additional optical members, such as a filter, may be optionally disposed between the first optical member and the EMR source.

DETAILED DESCRIPTION OF THE PREFERRED EMBODIMENTS

Figure 1A:
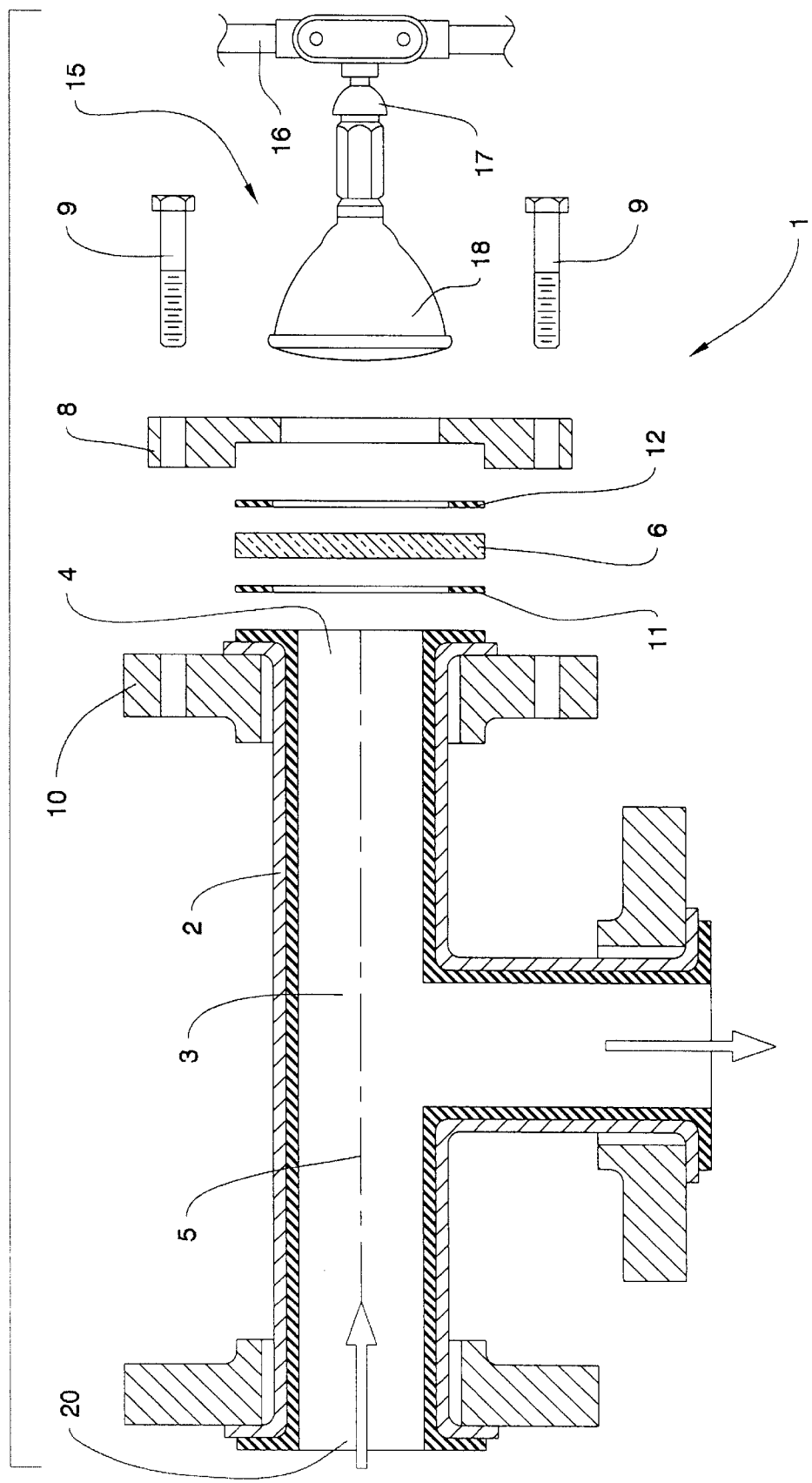
FIG. 1A is a cross-sectional exploded view of a first embodiment of the present invention.

Turning now to FIG. 1A, a first embodiment 1 of the present invention is shown in an exploded view as being connectable to a conduit 2 which may contain a fluid. For the purposes herein, this invention will likely find its greatest utility in chlorine production environments, wherein the fluid 3 is chlorine wet gas (chlorine having 150 ppm by weight or greater of water). In such environments, three of the various components of the chlorine stream of primary concern will be diatomic chlorine ($Cl_2$), diatomic hydrogen ($H_2$), and nitrogen trichloride ($NCl_3$), each of which may be subjected to photolytic fission. Use of the term "photolytic fission" is meant to include either homolytic fission (in the case of like atoms, such as in Cl$_2$) or heterolytic fission (in the case of dissimilar atoms, such as in NCl$_3$), as applicable. It will be appreciated to those of ordinary skill that the invention may be applied to any number of other environments where the fluid to be treated is something other than chlorine, and that the operational parameters of the invention may be altered to suit the particular needs of the fluid being treated. However, for the sake of simplicity, the remainder of this disclosure will provide a detailed explanation of the invention as applied to the treatment of chlorine.

Conduit 2 includes a longitudinal axis 5 and an opening 4 which would normally be closed by a blind flange (not shown). Installation of the first embodiment 1 involves an initial shut-down of the fluid flowing through conduit 2 (with subsequent air purging) so that removal of the blind flange can be accomplished with no safety hazard due to chlorine leaks. After removal of the blind flange from opening 4, an optical member 6 is sealably secured over opening 4 by an annular flange 7 having an aperture 8.

Optical member 6 may simply comprise a flat plate constructed from a material which is permeable to the EMR emitted by the EMR source, which will be described further herein. However, optical member 6 must also be strong enough to withstand the operating pressures of the system, such as the vacuum conditions within the conduit 2. For example, in the case of a chlorine production environment used in testing the invention, the optical member 6 was an annular edge sight glass constructed of Pyrex®, which is a registered trademark of Corning Glass Works (Glass Code 7740), having a thickness of ¾". The transmittance of the optical member 6 as used in testing was approximately 60%.

The diameter of aperture 8 should preferably be at least as large as the diameter of opening 4, but smaller than the diameter of optical member 6. Annular flange 7 is preferably constructed of plastic or other material resistant to chemical degradation and is tightened against optical member 6 using a plurality of bolts 9 engageable with conduit flange 10. First and second gaskets 11,12 are preferably constructed of tetrafluoroethylene (TFE), polytetrafluoroethylene (PTFE), or equivalent material and are installed on each side of optical member 6 in order to ensure a leak-proof seal and provide a cushioned surface when optical member 6 is held between conduit flange 10 and annular flange 7.

An EMR source 15 is positioned relative to the opening 4 such that the EMR emitted by the EMR source 15 is directed into the conduit 2. EMR source 15 is electrically connected to an external power supply 16, and may be supported by any external rack or support device 17. In order to achieve the maximum amount of exposure of the fluid 3 to the EMR, EMR source 15 should be positioned such that the EMR is directed primarily along the longitudinal axis 5 of the conduit 2. Generally, EMR source 15 may be any device, such as a lamp 18, adapted to emit EMR capable of causing photolytic fission of selected molecules. In a chlorine production environment, and in testing conducted by the inventor, a 100 Watt, Sylvania PAR 38 mercury vapor lamp, Model No. H44GS-100/M, was used. This particular lamp employs a parabolic aluminized reflector (PAR) and emits EMR at primary wavelengths (in nanometers, nm) of 334.2, 365.0, 404.7, 435.8, 546.1, and 578.0. Since it is known that the wavelength required to break the diatomic chlorine bond is approximately 495 nm, and that the wavelength required to break the nitrogen trichloride bond is approximately 598 nm, the EMR source 15 used in the experiments was clearly sufficient to reduce the levels of hydrogen and nitrogen trichloride in the tests, as summarized below.

The results of three testing runs are summarized in Table 1, wherein the temperature of the chlorine wet gas was approximately 80°–90° C. and flowing through a conduit at approximately 934 liters per minute. Note that one EMR source was used for Test Runs #1 and #2, but that two EMR sources were used for Test Run #3.

TABLE 1

| DATE | % H2 feed | % H2 outlet | % H2 Reduction | NCl3 In ppm | NCl3 Out ppm | % NCl3 Reduction |
|---|---|---|---|---|---|---|
| Test Run #1 One 100 Watt Bulbs on test skid | | | | | | |
| 05/23/95 | 1.19 | 1.190 | 0 | | | |
| 05/24/95 | 1.19 | 0.262 | 78 | 2.4 | 0.2 | 92 |
| 05/25/95 | 1.19 | 0.250 | 79 | 2.9 | 0.4 | 86 |
| 05/26/95 | 1.18 | 0.283 | 76 | 2.7 | 0.3 | 89 |
| 05/27/95 | 1.18 | 0.342 | 71 | 2.6 | 0.4 | 85 |
| 05/28/95 | 1.17 | 0.211 | 82 | 2.9 | 0.5 | 83 |
| 05/29/95 | 1.17 | 0.246 | 79 | 3.2 | 0.7 | 78 |
| 05/30/95 | 1.17 | 0.339 | 71 | 3.1 | 0.6 | 81 |
| 05/31/95 | 1.14 | 0.239 | 79 | 3 | 0.6 | 80 |
| 06/01/95 | 1.14 | 0.274 | 76 | 2.7 | 0.5 | 81 |
| 06/02/95 | 1.15 | 0.265 | 77 | 2.7 | 0.6 | 78 |
| 06/03/95 | 1.14 | 0.194 | 83 | 2.9 | 0.7 | 76 |
| 06/04/95 | 1.12 | 0.302 | 73 | 3.1 | 0.7 | 77 |
| Test Run #2 One 100 Watt Bulbs on test skid | | | | | | |
| 10/12/95 | 0.94 | 0.16 | 83 | 2.7 | 0.4 | 85 |
| 10/13/95 | 0.93 | 0.14 | 85 | 3 | 0.5 | 83 |
| 10/14/95 | 0.94 | 0.12 | 87 | 2.6 | 0.3 | 88 |
| 10/15/95 | 0.92 | 0.1 | 89 | 2.9 | 0.3 | 90 |
| 10/16/95 | 0.9 | 0.08 | 91 | 2.7 | 0.4 | 85 |
| 10/17/95 | 0.89 | 0.04 | 96 | 3.1 | 0.5 | 84 |
| 10/18/95 | 0.86 | 0 | 100 | 3 | 0.4 | 87 |
| 10/19/95 | 0.86 | 0 | 100 | 2.8 | 0.3 | 89 |
| 10/20/95 | 0.86 | 0 | 100 | 2.7 | 0.4 | 85 |
| 10/21/95 | 0.85 | 0 | 100 | 2.6 | 0.4 | 85 |
| 10/22/95 | 0.85 | 0 | 100 | 2.8 | 0.4 | 86 |
| Test Run #3 Two 100 Watt Bulbs on test skid | | | | | | |
| 11/10/95 | 1.05 | 0 | 100 | 3 | 0.1 | 97 |
| 11/11/95 | 1.05 | 0 | 100 | 2.9 | 0.1 | 97 |
| 11/12/95 | 1.05 | 0 | 100 | 2.8 | 0.1 | 96 |
| 11/13/95 | 1.04 | 0 | 100 | 3.3 | 0.2 | 94 |
| 11/14/95 | 1.04 | 0 | 100 | 3.1 | 0.1 | 97 |
| 11/15/95 | 1.04 | 0 | 100 | 3.3 | 0.2 | 94 |
| 11/16/95 | 1.04 | 0 | 100 | 3.2 | 0.2 | 94 |
| 11/17/95 | 1.04 | 0 | 100 | 2.9 | 0.1 | 97 |
| 11/18/95 | 1.03 | 0 | 100 | 2.7 | 0.1 | 96 |

As the results from Table 1 illustrate, both hydrogen and nitrogen trichloride were reduced significantly throughout Test Run #1 and throughout most of Test Run #2. However, a leak was discovered on Oct. 17, 1995, which introduced oxygen, which is a known chain reaction terminator, into the chlorine stream. After sealing the leak, Test Run #2 was resumed and hydrogen levels were undetectable, while the reduction of nitrogen trichloride levels remained about the same.

Figure 3:
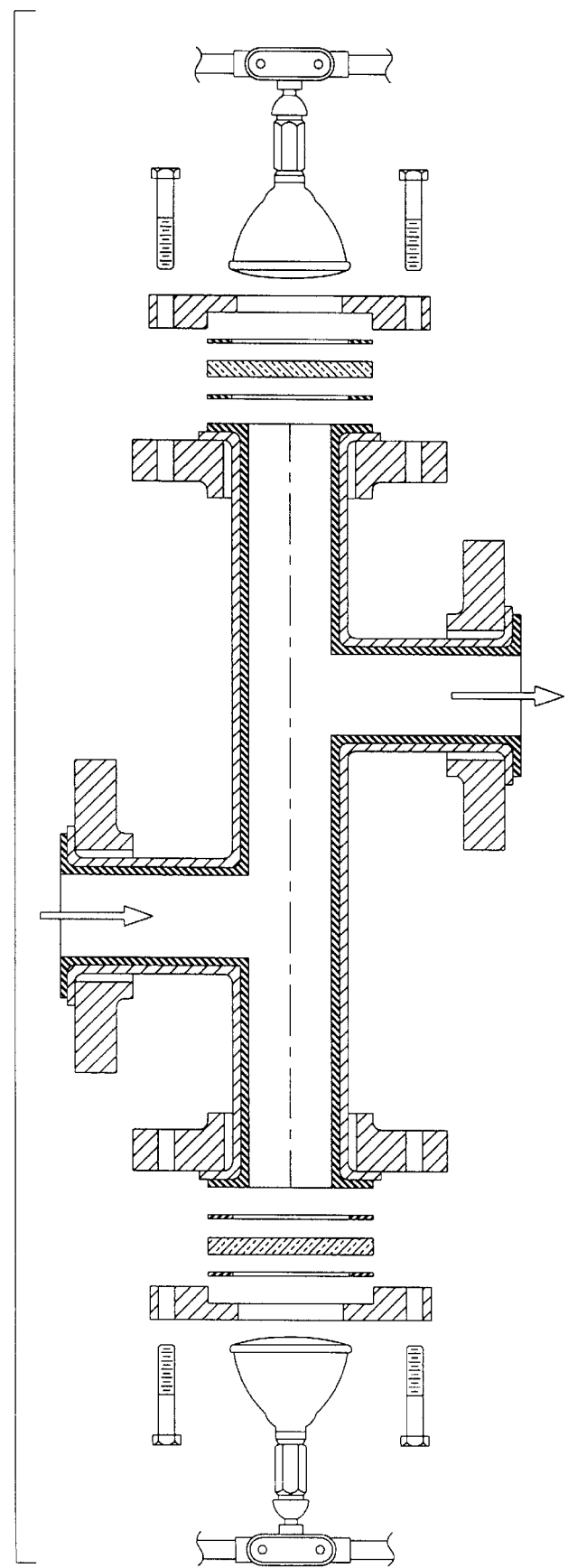
FIG. 3 is a cross-sectional exploded view of two identical embodiments of the invention used simultaneously.

Test Run #3 was run with two identical EMR sources, where the second EMR source was positioned at opening 20, similar to that shown in FIG. 3, and where the distance between the EMR sources was approximately two feet. During this test run, hydrogen levels were again undetectable, and the levels of nitrogen trichloride were reduced even further.

Figure 1B:
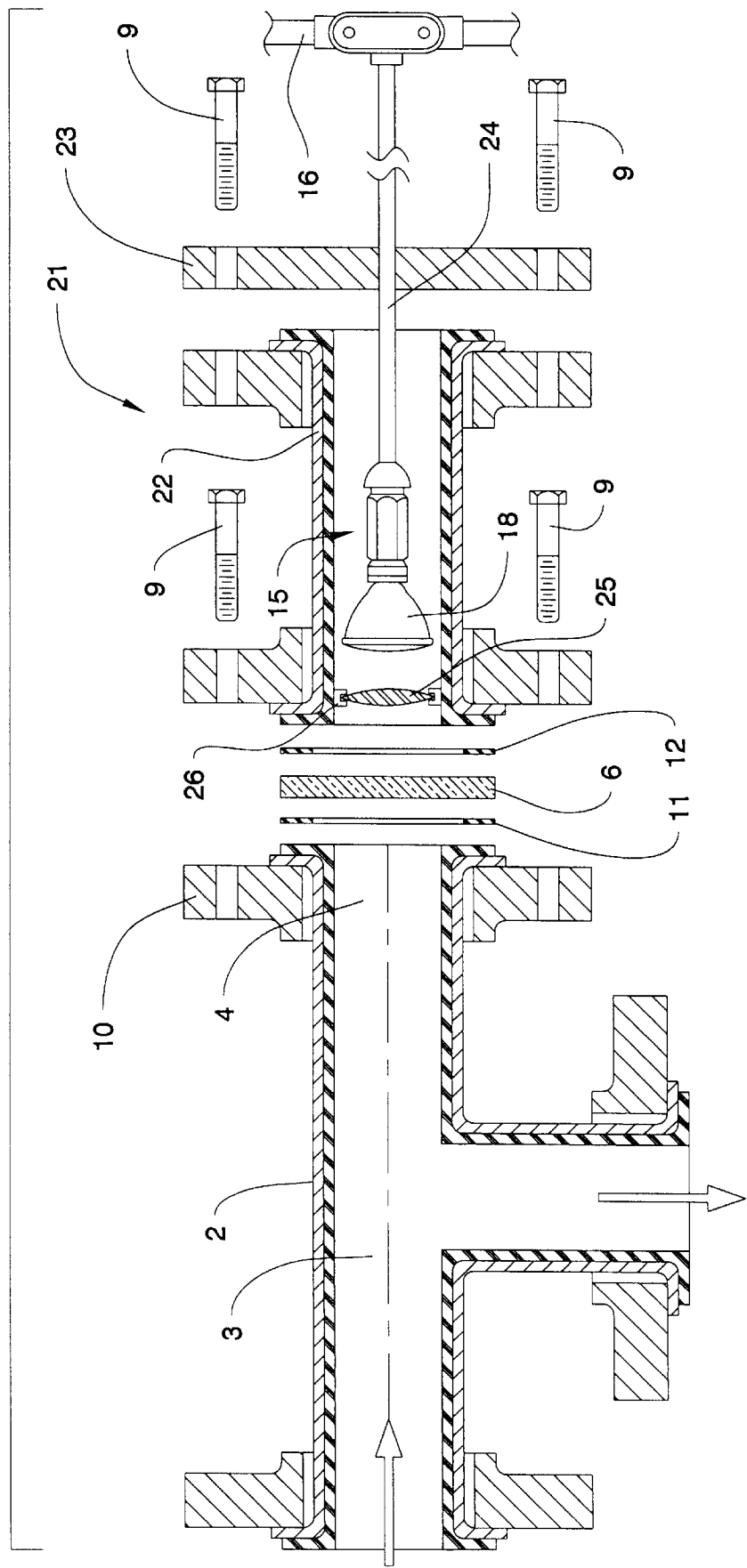
FIG. 1B is a cross-sectional exploded view of an alternate embodiment of the invention.

An alternate embodiment 21 of the invention is depicted in FIG. 1B, comprising a housing 22 which is attached to conduit flange 10 by bolts 9. EMR source 15 resides within housing 22 and is further bounded by a rear blind flange 23 and optical member 6. Thus, housing 22 may be construed as a virtual extension of conduit 2. Rear blind flange 23 is removably attachable to housing 22 by additional bolts 9, and includes means 24 for holding and supporting EMR source 15. This arrangement allows the EMR source 15 and rear blind flange 23 to be removed together as a unit so that the EMR lamp 18 may be easily replaced without disturbing the sealed relationship between conduit 2, optical member 6 and housing 22. Optionally, a second optical member 25, such as a convex lens, a concave lens, an EMR filter, or other optical element may be disposed between optical member 6 and EMR source 15 using appropriate fixation means 26 so that the EMR may be modified in accordance with one or more predetermined characteristics. For example, a filter may be used to subject the fluid only to EMR having a wavelength of 500 nm or higher, where only the nitrogen trichloride is subject to photolytic fission, as opposed to the diatomic chlorine.

Figure 2A:
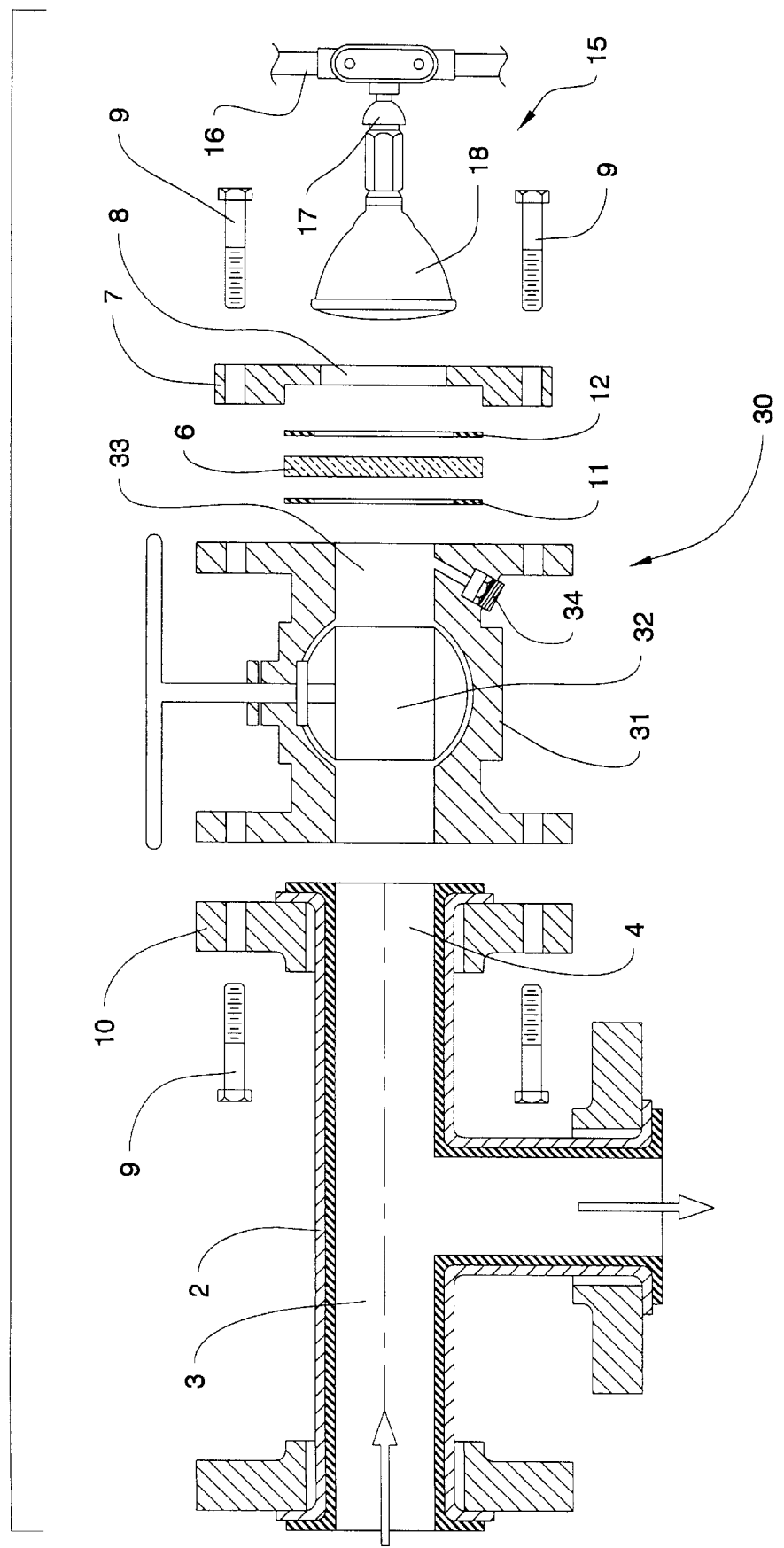
FIG. 2A is a cross-sectional exploded view of a preferred embodiment of the invention.

FIG. 2A depicts a preferred embodiment 30 of the present invention which is similar in many respects to the embodiment 1 of FIG. 1A, but wherein a valve 31 is disposed between the conduit 2 and optical member 6. Valve 31 may be any type of valve, such as a ball valve, butterfly valve or gate valve, which includes a passageway 32 allowing EMR to be transmitted through the passageway 32 and ultimately into the conduit 2. Passageway 32 leads into a second opening 33 which is sealed by optical member 6, gaskets 11,12, and annular flange 7 in the same manner as described earlier herein, except that annular flange 7 is bolted directly to valve 31. Thus, when valve 31 is open, EMR is directed from EMR source 15, through optical member 6 and passageway 32, and into conduit 2. When valve 31 is closed, no EMR may be transmitted to conduit 2, and optical member 6 may be removed for cleaning without interrupting the flow of fluid through the conduit system of the plant, resulting in tremendous savings in terms of labor and production. Preferably, an air purge valve 34 is fluidically connected between the valve 31 and optical member 6 so that chlorine or other fluid may be swept away from the passageway 32 and the vicinity of optical member 6 during the closing of valve 31 for maintenance operations. If desired, suitable automatic controls may be used in conjunction with valve 31 to enable immediate closure of valve 31 in the event of a breakage of optical member 6 or other pressure difference in its vicinity.

Figure 2B:
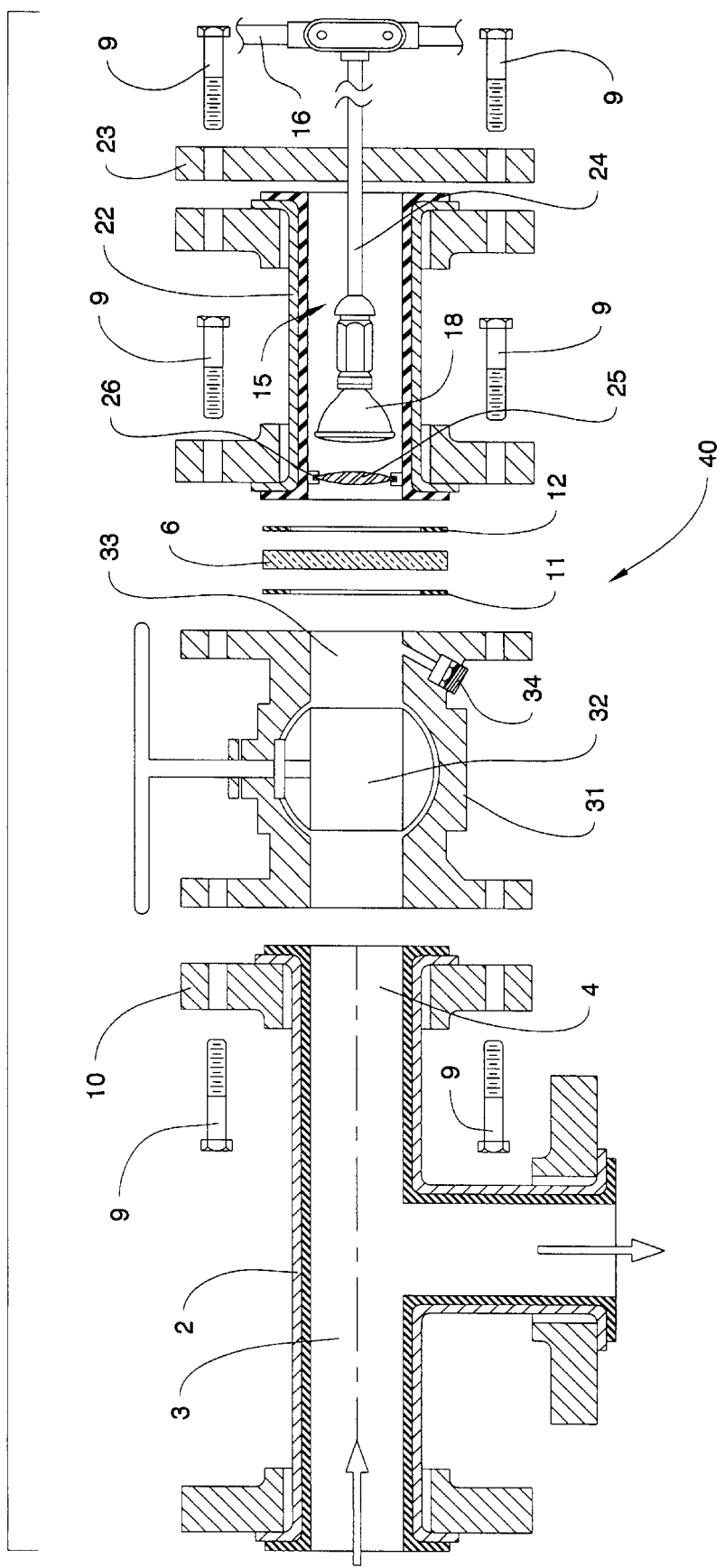
FIG. 2B is a cross-sectional exploded view of a more preferred embodiment of the invention.

FIG. 2B depicts a more preferred embodiment 40 of the present invention which combines the valve 31 of FIG. 2A with the features of FIG. 1B. The ability to remove and replace the EMR source 15 and/or change or add a second optical member 25 are available in this embodiment without having to interrupt the process flow, as explained earlier herein. Moreover, the valve 31 can be automated as described for FIG. 2A to protect the safety of plant personnel and others.

Finally, FIG. 3 depicts an arrangement in which two identical embodiments of FIG. 1A are employed to effectively double the effectiveness of the irradiation by directing EMR along the same longitudinal axis, but in opposite directions. As will be understood, any of the embodiments of FIGS. 1A–2B may be used in this configuration, either using identical embodiments or possibly mixing various embodiments, all with substantially identical effectiveness.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A device for irradiating a fluid containing molecules subject to photolytic fission within a conduit, wherein said conduit includes a first opening and a longitudinal axis, said device comprising:

(a) a valve fluidically connected to said first opening, said valve having a passageway leading to a second opening;

(b) a first optical member sealing said second opening;

(c) an electromagnetic radiation (EMR) source positioned relative to said first optical member such that said EMR is directed through said first optical member and said passageway and into said conduit when said valve is in an open position; and (d) air purge means, fluidically connected between said valve and said first optical member, for purging said fluid from the vicinity of said first optical member;

wherein said first optical member is constructed from a material which is permeable to said EMR.

2. The device of claim 1, wherein said EMR is directed primarily along the longitudinal axis of said conduit.

3. The device of claim 1, wherein said EMR source is adapted to emit EMR at a wavelength sufficient to cause photolytic fission of said molecules.

4. The device of claim 1, wherein said molecules include diatomic hydrogen, diatomic chlorine, and nitrogen trichloride, and wherein said EMR source is adapted to emit EMR at a wavelength sufficient to cause photolytic fission of said diatomic chlorine.

5. The device of claim 1, wherein said molecules include diatomic hydrogen, diatomic chlorine, and nitrogen trichloride, and wherein said EMR source is adapted to emit EMR at a wavelength sufficient to cause photolytic fission of said nitrogen trichloride.

6. The device of claim 1, wherein said second opening includes a flange, and wherein said EMR source is secured to said flange.

7. The device of claim 1, wherein said EMR source is removably attachable to said conduit while said first optical member remains sealably retained within said first opening.

8. The device of claim 1, further including a second optical member disposed between said first optical member and said EMR source, wherein said second optical member is adapted to modify said EMR in accordance with one or more predetermined characteristics.

* * * * *